United States Patent [19]

Grunwald

[11] 4,093,741

[45] June 6, 1978

[54] PROCESS FOR REDUCING BLOOD SUGAR CONCENTRATION IN A MAMMAL

[75] Inventor: Frederick A. Grunwald, Evansville, Ind.

[73] Assignee: Mead Johnson & Company, Evansville, Ind.

[21] Appl. No.: 734,154

[22] Filed: Oct. 20, 1976

Related U.S. Application Data

[62] Division of Ser. No. 604,971, Aug. 15, 1975, Pat. No. 3,998,879, which is a division of Ser. No. 478,497, Jun. 12, 1974, Pat. No. 3,917,692.

[51] Int. Cl.² ............................................. A61K 31/18
[52] U.S. Cl. ..................................................... 424/321
[58] Field of Search ........................................... 424/321

[56] References Cited

U.S. PATENT DOCUMENTS

| 3,298,917 | 1/1967 | Bicking | 424/321 |
| 3,917,718 | 11/1975 | Collins | 424/308 |

*Primary Examiner*—Jerome D. Goldberg
*Attorney, Agent, or Firm*—Robert H. Uloth; Robert E. Carnahan

[57] ABSTRACT

A new class of arylsulfonylcarbamoyl-1,3-cyclohexanediones and arylsulfonylcarbamoyl-1,3-dicarbonylacyclic compounds are disclosed. These substances have hypoglycemic or hyperglycemic properties and are of value in controlling abnormal blood sugar levels. The arylsulfonylcarbamoyl derivatives of 1,3-dicarbonylalicyclic and acyclic compounds are prepared by reacting an arylsulfonylisocyanate with a 1,3-dicarbonylalicyclic or acyclic reactant. Typical embodiments are 2-(N-p-chlorobenzenesulfonylcarbamoyl)-5,5-dimethylcyclohexane-1,3-dione and 5-(1-ethylpropyl)-2-(N-p-chlorobenzenesulfonylcarbamoyl)-1,3-cyclohexanedione.

6 Claims, No Drawings

PROCESS FOR REDUCING BLOOD SUGAR CONCENTRATION IN A MAMMAL

CROSS REFERENCE TO RELATED APPLICATION

This application is a divisional application of U.S. Pat. application Ser. No. 604,971 filed Aug. 15, 1975, and now U.S. Pat. No. 3,998,879, which in turn is a divisional application of U.S. Pat. application Ser. No. 478,497 filed June 12, 1974, and now U.S. Pat. No. 3,917,692.

BACKGROUND OF THE INVENTION

This invention pertains to carbon compounds having drug and bio-affecting properties. In particular, this invention relates to arylsulfonylcarbamoyl-1,3-dicarbonyl compounds effective in controlling blood sugar levels. Both chronic hypoglycemic and hyperglycemic states are known but the most prevalent condition found with regard to abnormal levels of blood sugar is that caused by diabetes which produces increased blood glucose levels. Various agents have been developed to lower blood sugar level for treatment of diabetes and among presently available antidiabetic agents there can be mentioned, by way of example, those of the sulfonylurea type such as tolubutamide. S. Hunig, et al., Chem. Ber., 95, 926 (1962) reported preparation of 2-(N-p-toluenesulfonylcarbamoyl)-cyclohexanone, a compound formally related to the compounds of the present invention, but discloses no biological properties therefor.

SUMMARY OF THE INVENTION

This invention relates generally to sulfonylcarbamoyl derivatives of 1,2-dicarbonyl compounds having blood sugar regulating properties. More particularly the invention pertains to arylsulfonyl-carbamoyl-1,3-cyclohexanediones characterized by Formula I, arylsulfonyl-carbamoyl-1,3-diacarbonlyacyclic compounds of Formula II and pharmaceutically acceptable basic salts thereof.

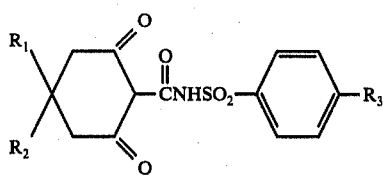

Formula I

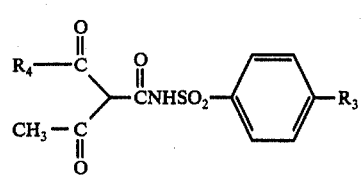

Formula II

In Formula I above, $R_1$ signifies a lower alkyl radical from 1 to 5 carbon atoms inclusive or phenyl; $R_2$ signifies hydrogen or a straight chain alkyl from 1 to 3 carbon atoms inclusive; and $R_1$ and $R_2$ taken together form $-(CH_2)_5-$. $R_3$ in Formulas I and II signifies hydrogen, halogen including chlorine, bromine, fluorine and iodine or lower alkyl from 1 to 4 carbon atoms inclusive. In Formula II, $R_4$ represents methyl, phenyl or benzyl.

It is to be understood that as used in this disclosure, the term "lower alkyl" comprehends both straight or branched chain hydrocarbon radicals such as methyl, ethyl, propyl, isopropyl, 1-butyl, 1-methylpropyl, 2-methylpropyl, tert.-butyl for those radicals containing 1 to 4 carbon atoms inclusive. Lower alkyl radicals containing 5 carbon atoms include pentyl and branched chain isomers thereof such as 3-methylbutyl, 1-methylbutyl, 1-ethylpropyl, 2,2-dimethylpropyl, and 1,1-dimethylpropyl.

By the term "pharmaceutically acceptable basic salts" as used herein, reference is made to salts of the Formula I and II compounds with alkaline agents. Said pharmaceutically acceptable basic salts of the above compounds are provided by admixture of Formula I or II compounds with substantially one chemical equivalent of an alkaline agent, such as for example, alkali metal alkoxides, alkali metal hydroxides, alkaline earth metal hydroxides, alkali metal carbonates, alkaline earth metal carbonates, alkali metal bicarbonates and alkaline earth metal bicarbonates.

A preferred method of a salt formation is to treat a compound of Formula I or II with substantially one chemical equivalent of sodium methoxide in methanol solution. The desired sodium salt precipitates from methanolic solution upon the addition of anhydrous ether or the solvent is removed by distillation.

The arylsulfonylcarbamoyl-1,3-dicarbonly compounds of the present invention characterized by Formulas I and II are prepared by a process which comprises reacting an alicyclic-1,3-dione or acyclic-1,3-dione selected from the group consisting of

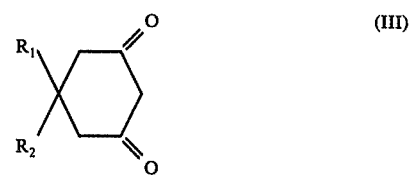

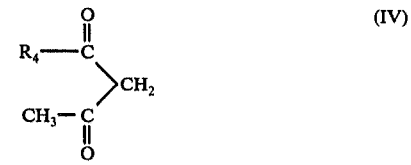

with a sulfonylisocyanate of Formula V

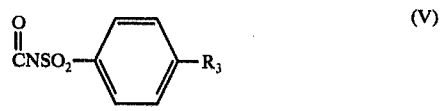

wherein $R_1$, $R_2$, $R_3$, and $R_4$ are as stated above in a suitable reaction inert solvent. The term "reaction inert solvent" as used herein refers to a solvent which functions as a diluent for the reaction and does not interact with the alicyclic or acyclic diketone or sulfonylisocyanate reactant. Benzene is a preferred solvent for carrying out the process but other solvents such as toluene, xylene, hexane, dioxane, tetrahydrofuran, 1,1-dichlorethane and the like are also satisfactory.

In carrying out the process of this invention for the preparation of compounds of the present invention, approximately equimolar quantities of the reactants are dissolved or suspended in the reaction inert solvent and the mixture maintained at a temperature of 0°–150° C. for a period of time ranging from 1 to 24 hours. The time period required for complete reaction is generally inversely proportional to the temperature at which the reaction is conducted, i.e., the higher the temperature, the shorter the reaction period.

Cyclohexanedione intermediates of Formula III are known or they can be prepared by means of a Michael Condensation involving diethylmaloanate and the appropriate α,β-unsaturated ketone according to the procedure of R. L. Frank and H. K. Hall, J. Am. Chem. Soc., 72, 1645 (1950).

The process of the present invention for regulating blood sugar concentration in a mammal comprises administering to a mammal requiring blood sugar concentration regulation an effective amount of a compound characterized by Formula I and II ranging from 3 to 200 mg./kg. body weight of said mammal to exert a blood sugar regulating effect. In the instant process, the compounds of the present invention are effective as hypoglycemic or hyperglycemic agents.

Oral administration of the compounds of the present invention is a particularly preferred form of administration but parenteral routes such as intramuscular, intravenous, intraperitoneal and subcutaneous administration may be employed. The compounds of the invention can be incorporated into pharmaceutical preparations such as tablets and capsules which contain the usual adjuvants and carriers such as talc, starch, lactose, magnesium stearate, and the like.

Conventional biological tests are employed to demonstrate blood sugar regulating properties of the compounds of the present invention characterized by Formulas I and II. For instance, the compounds of the invention administered orally to laboratory mammals such as guinea pig, rat, rabbit, and mouse provide a decrease or an increase in blood glucose concentration as determined by standard glucose assay described by W. S. Hoffman, J. Biol. Chem., 120, 51 (1937).

Significant hypoglycemic or hyperglycemic effects are obtained after an induction period of 1 to 2 hours when the compounds of the present invention are administered at a dose of 100 mg./kg. body weight. These effects are generally well-maintained for more than 8 hours post-drug administration.

Compounds of the present invention preferred for their hypoglycemic activity are:
5,5-Dimethyl-2-(N-p-toluenesulfonylcarbamoyl)-1,3-cyclohexanedione,
5-Ethyl-2-(N-p-toluenesulfonylcarbamoyl)-1,3-cyclohexanedione,
5-Isopropyl-2-(N-p-toluenesulfonylcarbamoyl)-1,3-cyclohexanedione,
5-tert.-Butyl-2-(N-p-toluenesulfonylcarbamoyl)-1,3-cyclohexanedione,
2-(N-p-Chlorobenzenesulfonylcarbamoyl)-5,5-dimethylcyclohexane-1,3-dione.

At a dose of 100 mg./kg. body weight, the compounds above provide a 20% decrease in blood sugar for a period of more than eight hours after the animals were treated. Compounds particularly preferred for long lasting hypoglycemic action are 5-isopropyl-(N-p-toluenesulfonylcarbamoyl)-1,3-cyclohexanedione and 2-(N-p-chlorobenzenesulfonylcarbamoyl)-5,5-dimethylcyclohexane-1,3-dione whereafter 8 hours decreased blood sugar level values of 34% and 36% respectively were obtained. Tolubutamide, by comparison, gave a 50% depression of the blood sugar level of rats one hour after dosing but 5 hours after dosing the blood sugar level had recovered to less than 20% below normal.

5-(1-Ethylpropyl)-2-(N-p-chlorobenzenesulfonylcarbamoyl)-1,3-cyclohexanedione is particularly preferred for its hyperglycemic activity. Oral administration of 5-(1-ethylpropyl)-2-(N-p-chlorobenzenesulfonylcarbamoyl)-1,3-cyclohexanedione to rats at a dose of 100 mg./kg. provides a marked hyperglycemic effect with a 25% elevation of blood sugar at 6 hours increasing to 44% in 8 hours.

The following examples are given by way of illustration and are not to be construed as limitations of this invention, variations of which are possible without departing from the scope and spirit thereof.

EXAMPLE 1

A mixture of 5,5-dimethyl-1,3-cyclohexanedione (7.0 g., 0.05 mole) and p-toluenesulfonylisocyanate (9.86 g., 0.05 mole) in 150 ml. of benzene is stirred at 40°–60° C. for a period of 6 hr. The mixture is then heated on a steam bath for 2 hr. and concentrated under reduced pressure providing a semi-solid residue which is taken up in a mixture of 45 ml. of acetone and 5 ml. of methanol. Addition of 10 ml. of water to the acetone-methanol solution provides a quantitative yield of product, m.p. 94°–108° C. Crystallization of the crude product from acetone-water affords 9.6 g. (56% yield) of 5,5-DIMETHYL-2-(N-p-TOLUENESULFONYLCARBAMOYL)-1,3-CYCLOHEXANEDIONE, m.p. 127.5°–129.5° C.

Analysis. Calcd. for $C_{16}H_{19}NO_3S$ (percent): C, 56.96; H, 5.68; S, 9.50. Found (percent): C, 57.23; H, 5.94; S, 9.61.

EXAMPLE 2

Reaction of equimolar amounts of 5-methyl-1,3-cyclohexanedione with p-toluenesulfonylisocyanate in benzene according to the procedure of Example 1 affords 5-METHYL-2-(N-p-TOLUENESULFONYLCARBAMOYL)-1,3-CYCLOHEXANEDIONE, m.p. 121.5°–122.5° C. (corr.).

Analysis. Calcd. for $C_{15}H_{17}NO_5S$ (percent): C, 55.71; H, 5.30; N, 4.33; S, 9.92. Found (percent): C, 55.80; H, 5.38; N, 4.52; S, 10.14.

EXAMPLE 3

Reaction of 5-ethyl-1,3-cyclohexanedione with p-toluenesulfonylisocyanate in benzene according to the procedure of Example 1 affords 5-ETHYL-2-(N-p-TOLUENESULFONYLCARBAMOYL)-1,3-CYCLOHEXANEDIONE, m.p. 86°–87° C. (corr.).

Analysis. Calcd. for $C_{16}H_{19}NO_5S$ (percent): C, 56,96; H, 5,68; N, 4.15; S, 9.50. Found (percent): C, 57.11; H, 5.74; N, 4.09; S, 9.79.

EXAMPLE 4

Reaction of 5-isopropyl-1,3-cyclohexanedione with p-toluenesulfonylisocyanate in benzene according to the procedure of Example 1 affords 5-ISOPROPYL-2-(N-p-TOLUENESULFONYLCARBAMOYL)-1,3-CYCLOHEXANEDIONE, m.p. 106.5°–107.5° C. (corr.).

Analysis. Calcd. for $C_{17}H_{21}NO_5S$ (percent): C, 58.10; H, 6.01; N, 3.99. Found (percent): C, 58.24; H, 5.71; N, 4.01.

EXAMPLE 5

Reaction of 5-tert.-butyl-1,3-cyclohexanedione with p-toluenesulfonylisocyanate in benzene according to the procedure of Example 1 affords 5-tert.-BUTYL-2-(N-p-TOLUENESULFONYLCARBAMOYL)-1,3-CYCLOHEXANEDIONE, m.p. 161.5°–163° C. (corr.).

Analysis. Calcd. for $C_{18}H_{23}NO_5S$ (percent): C, 59.16; H, 6.34; N, 3.83; S, 8.78. Found (percent): C, 59.43; H, 6.27; N, 3.79; S, 8.71.

EXAMPLE 6

Reaction of equimolar amounts of spiro[5.5]undecane-2,4-dione with p-toluenesulfonylisocyanate in benzene according to the procedure of Example 1 affords 3-[N-(p-TOLUENESULFONYL)CARBAMOYL]-SPIRO[5.5]UNDECANE-2,4-DIONE, m.p. 150.5°–152° C. (corr.).

Analysis. Calcd. for $C_{19}H_{23}NO_5S$ (percent): C, 60.46; H, 6.14; N, 3.71; S, 8.50. Found (percent): C, 60.75; H, 6.26; N, 3.69; S, 8.57.

EXAMPLE 7

Reaction of equimolar amounts of 5,5-dimethylcyclohexane-1,3-dione with p-chlorobenzenesulfonylisocyanate in benzene according to the procedure of Example 1 affords 2-(N-p-CHLOROBENZENESULFONYLCARBAMOYL)-5,5-DIMETHYLCYCLOHEXANE-1,3-DIONE, m.p. 103°–105.5° C. (corr.).

Analysis. Calcd. for $C_{15}H_{16}ClNO_5S$ (percent): C, 50.34; H, 4.51; S, 8.96. Found (percent): C, 50.12; H, 4.56; S, 9.10.

2-(N-p-Chlorobenzenesulfonylcarbamoyl)-5,5-dimethylcyclohexane-1,3-dione sodium salt is obtained by dissolving 2-(N-p-chlorobenzenesulfonylcarbamoyl)-5,5-dimethylcyclohexane-1,3-dione and a molar equivalent of sodium methoxide in methanol and removing the solvent under reduced pressure.

EXAMPLE 8

Reaction of equimolar amounts of 5-isopropyl-1,3-cyclohexanedione with p-chlorobenzenesulfonylisocyanate in benzene according to the procedure of Example 1 affords 2-(N-p-CHLOROBENZENESULFONYLCARBAMOYL)-5-ISOPROPYL-1,3-CYCLOHEXANEDIONE, m.p. 100.5°–101.5° C. (resolidified and melting at 183.5° C. with dec.)(corr.).

Analysis. Calcd. for $C_{16}H_{18}ClNO_5S$ (percent): C, 51.68; H, 4.88; N, 3.77; S, 8.62; Cl, 9.54. Found (percent): C, 51.90; H, 5.03; N, 3,92; S, 8.87; Cl, 9.84.

EXAMPLE 9

Reaction of equimolar amounts of 5,5-dimethyl-1,3-cyclohexanedione with benzenesulfonylisocyanate in benzene according to the procedure of Example 1 affords 5,5-DIMETHYL-2-(N-BENZENESULFONYLCARBAMOYL)1,3-CYCLOHEXANEDIONE, m.p. 101°–103° C. (corr.).

Analysis. Calcd. for $C_{15}H_{17}NO_5S$ (percent): C, 55.71; H, 5.30; N,4.23; S, 9.91. Found (percent): C, 55.81; H, 5.40; N, 4.37; S, 9.82.

EXAMPLE 10

Reaction of equimolar amounts of 5-(1-ethylpropyl)-1,3-cyclohexanedione with p-toluenesulfonylisocyanate in benzene according to the procedure of Example 1 affords 5-(1-ETHYLPROPYL)-2-(N-p-TOLUENESULFONYLCARBAMOYL)-1,3-CYCLOHEXANEDIONE, m.p. 111.5°–112.5° C. (corr.).

Analysis. Calcd. for $C_{19}H_{25}NO_5S$ (percent): C, 60.13; H, 6.64; N, 3.69; S, 8.45. Found (percent): C, 60.10; H, 6.61; N, 3.67; S, 8.57.

EXAMPLE 11

Reaction of equimolar amounts of 5-(1-ethylpropyl)1,3-cyclohexanedione with p-chlorobenzenesulfonylisocyanate in benzene according to the procedure of Example 1 affords 5-(1-ETHYLPROPYL)-2-(N-p-CHLOROBENZENESULFONYLCARBAMOYL)-1,3-CYCLOHEXANEDIONE, m.p. 121°–122° C. (corr.).

Analysis. Calcd. for $C_{18}H_{22}ClNO_5S$ (percent): C, 54.05; H, 5.55; N, 3.50; S, 8.87. Found (percent): C, 53.97; H, 5.58; N, 3.52; S, 9.10.

EXAMPLE 12

Reaction of equimolar amounts of 1-phenyl-1,3-butanedione with p-toluenesulfonylisocyanate in benzene according to the procedure of Example 1 affords 1-PHENYL-2-(N-p-TOLUENESULFONYLCARBAMOYL)-1,3-BUTANEDIONE, m.p. 113.5°–116.5° C. (corr.).

Analysis. Calcd. for $C_{18}H_{17}NO_5S$ (percent): C, 60.15; H, 4.77; S, 8.92. Found (percent): C,59.86; H, 4,81; S, 8.99.

EXAMPLE 13

Reaction of equimolar amounts of 2,4-pentanedione with p-toluenesulfonylisocyanate in benzene according to the procedure of Example 1 affords 3-(N-p-TOLUENESULFONYLCARBAMOYL)-2,4-PENTANEDIONE, m.p. 137°–139.5° C. (corr.).

Analysis. Calcd. for $C_{13}H_{15}NO_5S$ (percent): C, 52.51; H, 5.08; S, 10.78. Found (percent): C,52.65; H, 5.16; S, 10.79.

EXAMPLE 14

Reaction of equimolar amounts of 5-propyl-1,3-cyclohexanedione with p-toluenesulfonylisocyanate in benzene according to the procedure of Example 1 affords 5-PROPYL-2-(N-p-TOLUENESULFONYLCARBAMOYL)-1,3-CYCLOHEXANEDIONE, m.p. 132.5°–133.5° C. (corr.).

Analysis. Calcd. for $C_{17}H_{21}NO_5S$ (percent): C, 58.10; H, 6.01; N, 3.99; S, 9.12. Found (percent): C, 58.38; H, 6.11; N, 4.06; S, 9.04.

EXAMPLE 15

Reaction of equimolar amounts of 5-isopropyl1,3-cyclohexanedione with benzenesulfonylisocyanate in benzene according to the procedure of Example 1 affords 5-ISOPROPYL-2-(N-BENZENESULFONYLCARBAMOYL)-1,3-CYCLOHEXANEDIONE, m.p. 112.5°–114° C. (corr.).

Analysis. Calcd. for $C_{16}H_{19}NO_5S$ (percent): C, 56.95; H, 5.68; N, 4.15; S, 9.50. Found (percent): C, 57.03; H, 5.78; N, 4.11; S, 9.72.

EXAMPLE 16

Reaction of equimolar amounts of 5-sec.-butyl1,3-cyclohexanedione with p-toluenesulfonylisocyanate in benzene according to the procedure of Example 1 affords 5-sec.-BUTYL-2-(N-p-TOLUENESULFONYL- CARBAMOYL)-1,3-CYCLOHEXANEDIONE, m.p. 92°–93° C. (corr.).

Anaylsis. Calcd. for $C_{18}H_{23}NO_5S$ (percent): C, 59.16; H, 6.34; S, 8.77. Found (percent): C, 59.39; H, 6.55; S, 8.95.

EXAMPLE 17

Reaction of equimolar amounts of 5-sec.-butyl1,3-cyclohexanedione with p-chlorobenzenesulfonylisocyanate in benzene according to the procedure of Example 1 affords 5-sec.-BUTYL-2-(N-p-CHLOROBENZENESULFONYLCARBAMOYL)-1,3-CYCLOHEXANEDIONE, m.p. 106°–107° C. (corr.).

Analysis. Calcd. for $C_{17}H_{20}ClNO_5S$ (percent): C, 52.92; H, 5.22; S, 8.31; Cl,9.19. Found (percent): C, 52.82; H, 5.16; S, 8.45; Cl, 9.04.

EXAMPLE 18

Reaction of equimolar amounts of 5-isobutyl-1,3-cyclohexanedione with p-toluenesulfonylisocyanate in benzene according to the procedure of Example 1 affords 5-ISOBUTYL-2-(N-p-TOLUENESULFONYLCARBAMOYL)-1,3-CYCLOHEXANEDIONE, m.p. 128°–130° C. (corr.).

Analysis. Calcd. for $C_{18}H_{23}NO_5S$ (percent): C, 59.16; H, 6.34; N, 3.83; S, 8.77. Found (percent): C, 59.16; H, 6.41; N, 3.69; S, 8.81.

EXAMPLE 19

Reaction of equimolar amounts of 5-phenyl-1,3-cyclohexanedione with p-toluenesulfonylisocyanate in benzene according to the procedure of Example 1 affords 5-PHENYL-2-[N-p-TOLUENESULFONYLCARBAMOYL]-1,3-CYCLOHEXANEDIONE, m.p. 163.5°–166° C. (corr.).

Analysis. Calcd. for $C_{20}H_{19}NO_5S$ (percent): C, 62.32; H, 4.97; S, 8.32. Found (percent): C, 62.15; H,, 5.11; S, 8.48.

EXAMPLE 20

Reaction of the equimolar amounts of 1-phenyl-2,4-pentanedione with p-toluenesulfonylisocyanate in benzene according to the procedure of Example 1 affords 1-PHENYL-3-(N-p-TOLUENESULFONYLCARBAMOYL)-2,4-PENTANEDIONE, m.p. 119.5°–120.5° C. (corr.).

Analysis. Calcd. for $C_{19}H_{19}NO_5S$ (percent): C, 61.11; H, 5.13; N, 3.76. Found (percent): C, 60.94; H, 5.03; N, 3.76.

What is claimed is:

1. A process for reducing blood sugar concentration in a mammal which comprises administering to a mammal requiring blood sugar reduction an effective amount ranging from 3 to 200 mg./kg. body weight of said mammmal to exert a blood sugar reducing effect of a compound selected from the group consisting of 5,5-dimethyl-2-(N-p-toluenesulfonylcarbamoyl)-1,3-cyclohexanedione;

5-ethyl-2-(N-p-toluenesulfonylcarbamoyl)-1,3-cyclohexanedione;

5-isopropyl-2-(N-p-toluenesulfonylcarbamoyl)-1,3-cyclohexanedione;

5-tert.-butyl-2-(N-p-toluenesulfonylcarbamoyl)-1,3-cyclohexanedione;

2-(N-p-chlorobenzenesulfonylcarbamoyl)-5,5-dimethylcyclohexane-1,3-dione and pharmaceutically acceptable basic salts thereof.

2. The process of claim 1 wherein the compound employed is 5,5-dimethyl-2-(N-p-toluenesulfonylcarbamoyl)-1,3-cyclohexanedione.

3. The process of claim 1 wherein the compound employed is 5-ethyl-2-(N-p-toluenesulfonylcarbamoyl)-1,3-cyclohexanedione.

4. The process of claim 1 wherein the compound employed is 5-isopropyl-2-(N-p-toluenesulfonylcarbamoyl)-1,3-cyclohexanedione.

5. The process of claim 1 wherein the compound employed is 5-tert.-butyl-2-(N-p-toluenesulfonylcarbamoyl)-1,3-cyclohexanedione.

6. The process of claim 1 wherein the compound employed is 2-(N-p-chlorobenzenesulfonylcarbamoyl)-5,5-dimethylcyclohexane-1,3-dione.

* * * * *